(12) United States Patent
Pang et al.

(10) Patent No.: US 10,987,298 B2
(45) Date of Patent: Apr. 27, 2021

(54) MASCARA COMPOSITIONS COMPRISING A POLYMER HAVING CYCLIC AMIDE, CYCLIC AMINE AND ACRYLAMIDE FUNCTIONALITY

(71) Applicant: L'OREAL, Paris (FR)

(72) Inventors: Christopher Pang, New York, NY (US); Chunhua Li, Hillsborough, NJ (US); Jody Ebanks, Bloomfield, NJ (US); XianZhi Zhou, Millburn, NJ (US)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 16/022,820

(22) Filed: Jun. 29, 2018

(65) Prior Publication Data

US 2020/0000703 A1  Jan. 2, 2020

(51) Int. Cl.
| | | |
|---|---|---|
| *A61Q 1/00* | (2006.01) |
| *A61K 8/34* | (2006.01) |
| *A61K 8/41* | (2006.01) |
| *A61K 8/86* | (2006.01) |
| *A61K 8/891* | (2006.01) |
| *A61K 8/42* | (2006.01) |
| *A61K 31/79* | (2006.01) |
| *A61K 8/81* | (2006.01) |
| *A61K 8/895* | (2006.01) |
| *A61Q 1/10* | (2006.01) |

(52) U.S. Cl.
CPC ............ *A61K 8/8158* (2013.01); *A61K 8/34* (2013.01); *A61K 8/8182* (2013.01); *A61K 8/891* (2013.01); *A61K 8/895* (2013.01); *A61Q 1/10* (2013.01)

(58) Field of Classification Search
CPC ........... A61Q 1/00; A61Q 1/10; C08F 226/10; C08F 220/156; C08F 226/08; C08F 26/10; A61K 2800/10; A61K 8/8176; A61K 8/8182; A61K 8/8158; A61K 2800/594; A61K 8/8152; A61K 8/8147; A61K 8/891; A61K 8/34; A61K 8/86; A61K 8/41
See application file for complete search history.

(56) References Cited

U.S. PATENT DOCUMENTS

| | | | |
|---|---|---|---|
| 6,517,823 B1 | 2/2003 | Norman et al. | |
| 7,504,093 B2 | 3/2009 | Bracken et al. | |
| 2002/0085986 A1* | 7/2002 | De La Poterie | A61K 8/044 424/70.11 |
| 2010/0218781 A1* | 9/2010 | McNamara | A45D 40/26 132/200 |
| 2015/0079016 A1* | 3/2015 | Bolognini | A61K 8/8152 424/70.7 |
| 2017/0035679 A1 | 2/2017 | Douezan et al. | |
| 2017/0065512 A1 | 3/2017 | Zhu et al. | |

FOREIGN PATENT DOCUMENTS

| | | | | |
|---|---|---|---|---|
| EP | 1690523 A1 * | 8/2006 | ........... | A61K 8/0241 |
| WO | 2010014328 | 2/2010 | | |
| WO | 2017044546 | 3/2017 | | |

\* cited by examiner

*Primary Examiner* — Tracy Liu
(74) *Attorney, Agent, or Firm* — Meagher Emanuel; Laks Goldberg & Liao, LLP.

(57) ABSTRACT

A mascara composition includes a vehicle comprising water; a primary film-forming polymer that is a non-ionic and water-soluble or water dispersible copolymer comprising a first cyclic amide monomer, a cyclic amine monomer, and an acrylamide monomer; at least one nonionic secondary film-forming polymer having a fraction of a second cyclic amide monomer that is at least about 70% by weight of the at least one secondary film-forming polymer; and from about 0.5% to about 8% by weight of a C2-C5 alcohol.

17 Claims, No Drawings

MASCARA COMPOSITIONS COMPRISING A POLYMER HAVING CYCLIC AMIDE, CYCLIC AMINE AND ACRYLAMIDE FUNCTIONALITY

FIELD OF THE INVENTION

The present invention relates to a cosmetic composition for keratinous materials such as keratin fibers. The cosmetic composition is preferably a mascara composition for eyelashes.

DISCUSSION OF THE BACKGROUND

Mascara compositions are commonly used to enhance the appearance of eyelashes. Conventional mascara compositions generally use waxes to form crystalline network structures to enhance curl, volume, length, thickness, and/or colors to eyelashes. However, mascara compositions that derive their performance primarily from waxes tend to become less resistant to oil and/or sebum, causing smearing, flaking, and/or color transferring after wearing for a certain amount of time. Furthermore, while conventional wax-based mascara can be used to assist in moderate curl formation eyelashes, users of mascara typically are forced to rely on particular applicators or eyelash curling devices to enhance curl to any substantial degree.

The inventors of the present have found that certain mascara formulations are actually useful for inducing a curling effect and lastingness to eyelashes as compared to conventional mascara formulations.

Accordingly, one aspect of the present invention is a mascara composition which is able to impart an enhanced appearance to the eyelashes by enhancing eyelash curling. Another aspect of the present invention is directed to a method of making up eyelashes to enhance physical appearance of the eyelashes.

SUMMARY OF THE INVENTION

According to certain embodiments of the present invention, a mascara composition includes a vehicle comprising water, a primary film-forming polymer, a nonionic secondary film-forming polymer and from about 0.5% to about 8% of a C2-C5 alcohol. The primary film-forming polymer is or includes a non-ionic water-soluble or water dispersible copolymer comprising a cyclic amide monomer, a cyclic amine monomer, and an acrylamide monomer. The nonionic secondary film-forming polymer has a fraction of a second cyclic amide monomer that is at least about 70% by weight of the nonionic secondary film-forming polymer. The mascara composition may be substantially free of wax.

According to certain other aspects of the present invention, a mascara composition, includes from about 40% to about 90% by weight of water. It further includes a primary film-forming polymer that is a non-ionic and water-soluble or water dispersible copolymer comprising a first cyclic amide monomer, a cyclic amine monomer, and an acrylamide monomer. It further includes a first secondary film-forming polymer having a fraction of a second cyclic amide monomer that is at least about 70% by weight, wherein the at least one secondary film-forming polymer is non-ionic. It further includes a second secondary film-forming polymer which is a dimethicone copolymer. It further includes from about 0.5% to about 8% by weight of ethanol. The mascara composition may be substantially free of wax.

It is to be understood that both the foregoing general description and the following detailed description are exemplary and explanatory only, and are not restrictive of the invention.

DETAILED DESCRIPTION OF THE INVENTION

Unless otherwise indicated, all numbers expressing quantities of ingredients and/or reaction conditions are to be understood as being modified in all instances by the term "about." Accordingly, unless indicated to the contrary, the numerical parameters set forth in the following specification and attached claims are approximations that may vary depending upon the desired properties sought to be obtained by the present invention.

As used herein, the expression "at least one" means one or more and thus includes individual components as well as mixtures/combinations.

Other than in the operating examples, or where otherwise indicated, all numbers expressing quantities of ingredients and/or reaction conditions are to be understood as being modified in all instances by the term "about," meaning within 10% to 15% of the indicated number, and, in certain embodiments within 0% to 5% of the indicated number. Further numerical ranges are meant to include all combinations and sub-combinations. For example, from about 5%, 10% or 15% to about 20%, 50% or 60% means about 5% to about 20%, about 5% to about 50%, about 5% to about 60%, about 10% to about 20%, about 10% to about 50%, about 10% to about 60%, about 15% to about 20%, about 15% to about 50%, or about 15% to about 60%.

As used herein, "mascara" and "mascara composition" mean a composition that is intended to be applied to keratinous materials, preferably keratin fibers, in particular eyelashes and/or eyebrows, further in particular eyelashes.

As used herein, "keratinous materials" include, but are not limited to, skin, nail, living keratin fibers such as head hair, eyelashes, and eyebrows, and non-living keratin fibers such as swatches, extensions, and false eyelashes. The living and non-living keratin fibers include any mammalian hair, including human hair.

"Percent" or "%" as used herein, when referring to concentrations of ingredients or components in compositions refers to percent by weight. Unless otherwise specifically stated, the percent of a particular ingredient or ingredients is on a solids basis and is relative to the entire mascara composition.

"Solids basis" or "actives basis" refers to the amount of a particular ingredient exclusive of any solvents, carriers, impurities and the like that may be supplied with the particular ingredient "Substantially free" as used herein to refer to the presence of ingredients within compositions of the present invention, means that the particular ingredient is present in concentrations by weight of less than about 1%, such as less than about 0.5%, such as less than about 0.25%, such as about 0%.

"Substituted" as used herein, means comprising at least one substituent. Non-limiting examples of substituents for substitution include atoms, such as oxygen atoms and nitrogen atoms, as well as functional groups, such as hydroxyl groups, ether groups, alkoxy groups, acyloxyalky groups, oxyalkylene groups, polyoxyalkylene groups, carboxylic acid groups, amine groups, acylamino groups, amide groups, halogen containing groups, ester groups, thiol groups, sulphonate groups, thiosulphate groups, siloxane groups, and polysiloxane groups. The substituent(s) may be further substituted.

The term "self-curling" refers to an attribute associate with compositions of the present invention. Self-curling refers to the ability of a composition to induce curling on eyelashes upon drying—and not from use of an applicator that is specifically to induce curling. Self-curling may be measured using the SELF CURLING TEST noted in this specification.

Mascara Composition

According to the present invention, the inventors have found that particular mascara compositions comprising a film-forming polymer portion have surprising and unexpected properties such as those related to self-curling. These compositions include a film-forming polymer portion that include a vehicle comprising water; a primary film-forming polymer that is a non-ionic and water-soluble or water dispersible copolymer comprising a first cyclic amide monomer, a cyclic amine monomer, and an acrylamide monomer; at least one nonionic secondary film-forming polymer having a fraction of a second cyclic amide monomer that is at least about 70% by weight of the at least one nonionic secondary film-forming polymer; and from about 0.5% to about 8% by weight of a C2-C5 alcohol. Without wishing to be bound by theory, it is believed that the presence of moderate amounts of the C2-C5 alcohol promotes good film formation and an appropriate rate of film shrinking upon drying, thereby enhancing the self-curling effect.

Film-Forming Polymer Portion

Mascara compositions of the present invention include a film-forming polymer portion that includes one or more film-forming polymers. One of ordinary skill in the art will readily appreciate the term "film-forming polymer" refers or "film forming agent" as used herein means a polymer or resin that leaves a film (e.g., a continuous film) on the substrate to which it is applied, for example, after a solvent accompanying the film former has evaporated, absorbed into and/or dissipated on or from the substrate. In order to evaluate whether a polymer is a film forming polymer a drawdown test may be performed by putting 5 to 10 grams of material on the center of a Leneta card stock (Black and White Opacity card Chart 2812 available from BYK Additives and Instruments of Geretsried, Germany) and using a 3 mil Drawdown Birdbar (also from Byk), spreading the material for across the sheet (8 in by 3 in) and allowing it to dry overnight. If the material forms a conformal coating and/or can picked up or scraped off with a razorblade to be removed as a free standing film, then it is film forming. Regardless, if it does not coat the card, cannot in any reasonable way be removed as a free-standing film and/or forms a loose powdery coating that rubs off readily onto one's finger, then it is not a film former. Film-forming polymers that are cosmetically or dermatologically acceptable may be utilized in the present invention. As used herein, "cosmetically acceptable" or "dermatologically acceptable" is intended to mean that a composition is suitable for use in contact with human tissues such as keratinous materials and mucous membranes without undue toxicity, incompatibility, instability, and/or allergic response.

The film forming polymer portion includes a film-forming polymer that is a non-ionic and water-soluble or water-dispersible copolymer comprising a cyclic amide monomer, a cyclic amine monomer, and an acrylamide monomer. Accordingly, the film-forming polymer that is a non-ionic and water-soluble or water-dispersible copolymer comprising a cyclic amide monomer, a cyclic amine monomer, and an acrylamide monomer will have cyclic amide, cyclic amine and acrylamide functionality. For clarity, by "non-ionic and water-soluble or water-dispersible" it is meant that the copolymer is non-ionic. The copolymer is also (either) water-soluble or water-dispersible, particularly to the extent that it can be readily stabilized throughout the vehicle of the composition.

Cyclic amide and cyclic amine monomers useful in film-forming polymers of the present invention include those having one or more aromatic or aliphatic ring structures. These rings may have sizes ranging from about having sizes of, for example, 5 to 8 ring members.

In certain embodiments of the invention, monomers useful in forming the film-forming polymers present in compositions of the present invention are polymerizable ethylenically unsaturated monomers having a cyclic amine residue or a cyclic amide residue. Accordingly, the cyclic amide monomers of the film-forming polymers useful in the present invention may include cyclic amide residues that are or include heterocyclic ring structures such as lactams and the like. These may include α-Lactam, β-lactam, γ-lactam, δ-lactam, and ε-lactam. In one notable embodiment, the cyclic amide is selected from a pyrrolidone (a γ-lactam) a caprolactam, and combinations thereof. Useful cyclic amine residues may include any of various heterocyclic amines such as azoles, pyrroles, pyrrolidines, carbamates, and the like. In one notable embodiment, the cyclic amine residue is an imidazole.

In certain other embodiments, acrylamide monomers useful according to the present invention include those having —$C_3H_5NO$ functional groups. Examples include (meth) acrylamides.

In certain embodiments, the non-ionic, water-soluble or water-dispersible copolymer comprising a cyclic amide monomer, a cyclic amine monomer, and an acrylamide monomer has a weight average molecular weight in a range from about 10,000 daltons to about 1,000,000 daltons.

In certain embodiments, the non-ionic, water-soluble or water-dispersible copolymer comprising a cyclic amide monomer, a cyclic amine monomer, and an acrylamide monomer may be a commercially available variety, such as LUVISET CLEAR AT3, a copolymer of N-vinyl pyrrolidone, methacrylamide, and N-vinylimidazole commercially available from BASF of Ludwigshafen, Germany.

The concentration of the non-ionic, water-soluble or water-dispersible copolymer comprising a cyclic amide monomer, a cyclic amine monomer, and an acrylamide monomer in the mascara composition may be greater than about 7%. In certain embodiments the concentration is greater than about 10%, such as greater than about 15%. In certain other embodiments, compositions of the present invention include the non-ionic, water-soluble or water-dispersible copolymer comprising a cyclic amide monomer, a cyclic amine monomer, and an acrylamide monomer in a concentration from about 5%, 10% 15% or 20% to about 20%, 30%, 40% 50% or 60% including all combinations of such ranges.

According to certain embodiments of the invention, the film-forming polymer portion includes a primary film-forming polymer. By "primary film-forming polymer," it is meant the film forming polymer or class thereof that comprises 50% or more of the entire film forming polymer portion. According to certain notable embodiments, the non-ionic, water-soluble or water-dispersible copolymer comprising a cyclic amide monomer, a cyclic amine monomer, and an acrylamide monomer is the primary film forming polymer.

According to certain embodiments the non-ionic, water-soluble or water-dispersible copolymer including a cyclic amide monomer, a cyclic amine monomer, and an acrylamide monomer comprises 55% percent or more by weight of the film-forming polymer portion, such as about 60% to about 95%, such as about 75% to about 95% of the film-forming polymer portion.

The film-forming polymer portion also includes one or more secondary film-forming polymers. By "secondary" film-forming polymers it is meant that the combined concentration of these one or more secondary film-forming polymers in the mascara composition is less than the concentration of the primary film-forming polymer. In certain embodiments, the one or more secondary film forming polymers comprise 5% to about 25% of the film-forming polymer portion.

At least one of the one or more secondary film forming polymers is nonionic and includes cyclic amide monomer (herein after "second cyclic amide monomer"). The fraction (e.g., weight fraction) of the second cyclic amide monomer in the nonionic secondary film forming polymer is at least about 70%. The second cyclic amide monomer may again be selected from a vinyl pyrrolidone (a γ-lactam) a caprolactam, and combinations thereof.

In certain other embodiments of the invention, the nonionic secondary film-forming polymer having a fraction of a second cyclic amide monomer that is at least about 70% comprises a first nonionic secondary film-forming polymer having vinyl pyrrolidone functionality and a second nonionic secondary film-forming polymer having vinylcaprolactam functionality.

In certain other embodiments, the nonionic secondary film-forming polymer having a fraction of a second cyclic amide monomer that is at least about 70% comprises a first nonionic secondary film-forming polymer having vinyl pyrrolidone functionality and a second nonionic secondary film-forming polymer having vinylcaprolactam functionality. The concentration by weight of the first nonionic secondary film-forming polymer having vinyl pyrrolidone functionality in the mascara is less than the concentration by weight in the mascara of the second nonionic secondary film-forming polymer having vinylcaprolactam functionality.

Suitable examples of the at least one of the one or more nonionic secondary film forming polymers are vinyl pyrrolidone/vinyl acetate copolymers having at least 70% vinyl pyrrolidone monomer, such as LUVIKSOL 73E, LUVIKSOL 73W. Other suitable examples include polyvinylcaprolactam, such as LUVIKSOL Plus. Yet other suitable examples include polyvinyl pyrrolidone homopolymer such as PVP K-60 (or PLASDONE K-60), PVPK-90 (or PLASDONE K-90), or PVP K-120 (or PLASDONE K-120), each commercially available from Ashland, Inc of Kovington, Ky.

In certain embodiments, the composition may include additional secondary film forming polymers such as a dimethicone copolymer such as a non-ionic dimethicone copolymer. The dimethicone copolymer may be particles dispersed in an aqueous dispersion medium. Non-limiting examples of useful nonionic silicone polymers include polymethylsiloxane resin, a linear block copolymer, and a mixture thereof. In certain embodiments, the dimethicone copolymer is a copolymer of dimethylpolysiloxane and vinyl dimethylpolysiloxane (i.e., a polydimethylsiloxane/vinyl copolymer or a copolymer of dimethylpolysiloxane and an acrylate. The dimethicone copolymer may be crosslinked or end-capped with functional groups. For example, a polydimethylsiloxane and vinyl dimethylpolysiloxane may comprise dimethylpolysiloxane that is crosslinked with vinyl dimethylpolysiloxane and/or dimethylpolysiloxane that is end-capped with vinyl dimethylpolysiloxane. In a notable embodiment the dimethylpolysiloxane that is crosslinked with vinyl dimethylpolysiloxane. In certain other embodiments the dimethicone copolymer is included in the at least one secondary film forming polymer and the film-forming polymer having a fraction of a second cyclic amide monomer that is at least about 70% by weight is optional.

An example of a particularly useful dimethicone copolymer is a divinyl-dimethicone/dimethicone copolymer available as DOWSIL HMW 2220 Non-Ionic Emulsion, available from Dow Corning of Midland, Mich. This is a 60 percent active aqueous dispersion of divinyldimethicone/dimethicone copolymer and comprising $C_{12}$-$C_{13}$ Pareth-3 and $C_{12}$-$C_{13}$ Pareth-23.

The amount of dimethicone copolymer be less than about 2%, such as less than about 1%, such as from about 0.1, 0.2, or 0.3% to about 0.4%, 0.5% or 1% in the mascara.

In certain embodiments, the composition may include yet additional secondary film forming polymers (such as those not necessarily including the second cyclic amide monomer) including any of those that are commonly used in mascara compositions such as non-crosslinked acrylate and acrylic co-polymers, urethane polymers, polyesters. A non-limiting example of a suitable non-crosslinked secondary film-forming polymer is sodium alginate, available as PROTANAL PH 6160 from FMC Health and Nutrition of Philadelphia, Pa.

The primary film-forming polymer and the at least one secondary film-forming polymer make up a film forming polymer portion of the mascara composition. In certain embodiments, the primary film-forming polymer portion comprises about 60% to about 95% by weight of the primary film-forming polymer and from about 5% to about 40% of the at least one secondary film-forming polymer.

For example, in certain embodiments of the invention, the film-forming polymer portion comprises from about 60% to about 95% by weight of a copolymer of N-vinyl pyrrolidone, methacrylamide, and N-vinylimidazole; from about 9% to about 25% by weight of a nonionic film-forming polymer having a fraction of a second cyclic amide monomer that is at least about 70% (e.g., a vinyl pyrrolidone/vinyl acetate copolymer or a polyvinylcaprolactam). In certain other embodiments the film-forming polymer portion further comprises from about 1% to about 3% by weight of a dimethicone copolymer.

Furthermore, in certain other embodiments, the composition is substantially free of charged polymers such as cationic polymers.

C2-C5 Alcohol

Mascaras of the present invention further include a C2-C5 alcohol, preferably a C2-C5 alcohol monoalcohol, such as ethanol or isopropanol. The concentration of the C2-C5 alcohol is from about 0.5% by weight to about 8% by weight, such as about 1% by weight to about 6% by weight.

Wax

Compositions of the present invention may include wax. As used herein, "wax" is intended to mean a lipophilic fatty compound that is solid at room temperature (about 25° C.) and atmospheric pressure (760 mmHg, i.e., 105 Pa), which undergoes a reversible solid/liquid change of state and which has a melting point of greater than 30° C., and in some embodiments, greater than about 55° C. up to about 120° C. or even as high as about 200° C.

The term wax may include waxes of animal origin, waxes of plant origin, waxes of mineral origin and waxes of synthetic origin. Examples of waxes of animal origin include beeswaxes, lanolin waxes and Chinese insect waxes. Examples of waxes of plant origin include rice waxes, carnauba wax, candelilla wax, ouricurry wax, cork fiber waxes, sugar cane waxes, Japan waxes, sumach wax and cotton wax. Examples of waxes of mineral origin include paraffins, microcrystalline waxes, montan waxes and ozokerites. Examples of waxes of synthetic origin include polyolefin waxes, e.g., polyethylene waxes, waxes obtained by Fischer-Tropsch synthesis, waxy copolymers and their esters, and silicone and fluoro waxes.

The term wax may further include high melting point hydrogenated oils of animal or plant origin. Examples include hydrogenated jojoba waxes and hydrogenated oils which are obtained by catalytic hydrogenation of fats composed of a $C_8$-$C_{32}$ linear or nonlinear fatty chain, hydrogenated sunflower oil, hydrogenated castor oil, hydrogenated copra oil, hydrogenated lanolin and hydrogenated palm oils.

In certain embodiments, compositions of the present invention include wax, such as from about 0.5%, 2% or 4% to about 5%, 10% or 20% including all combinations of such ranges. However, in certain notable embodiments, compositions of the present invention are substantially free of wax.

Oil

Compositions of the present invention may include oils. However, in certain notable embodiments, compositions of the present invention are substantially free of oils. In certain particular embodiments, compositions of the present invention have less than 0.25% of waxes and less than 0.25% of oils.

As used herein, by "oils," it is meant compounds having a melting point of less than about 30 C and generally insoluble in water and includes a hydrophobic moiety, such as one meeting one or more of the following three criteria: (a) has a carbon chain of at least six carbons in which none of the six carbons is a carbonyl carbon or has a hydrophilic moiety (defined below) bonded directly to it; (b) has two or more alkyl siloxy groups; or (c) has two or more oxypropylene groups in sequence. The hydrophobic moiety may include linear, cyclic, aromatic, saturated or unsaturated groups. The hydrophobic compound is in certain embodiments not amphiphilic and, as such, in this embodiment does not include hydrophilic moieties, such as anionic, cationic, zwitterionic, or nonionic groups, that are polar, including sulfate, sulfonate, carboxylate, phosphate, phosphonate, ammonium, including mono-, di-, and trialkylammonium species, pyridinium, imidazolinium, amidinium, poly(ethyleneiminium), ammonioalkylsulfonate, ammonioalkylcarboxylate, amphoacetate, and poly(ethyleneoxy)sulfonyl moieties. In certain embodiments, the oil does not include hydroxyl moieties.

Suitable examples of compounds of oils include vegetable oils (glyceryl esters of fatty acids, triglycerides) and fatty esters. Specific non-limiting examples include, without limitation, esters such as isopropyl palmitate, isopropyl myristate, isononyl isonanoate $C_{12}$-$C_{15}$ alkyl benzoates, caprylic/capric triglycerides, silicone oils (such as dimethicone and cyclopentasiloxane), pentaerythritol tetraoctanoate and mineral oil. Other examples of oils include liquid organic ultraviolet filter commonly used for example as UV-absorbing sunscreens such as octocrylene, octyl salicylate, octyl methoxyxcinnamate, among others.

In certain embodiments, compositions of the present invention include oils, such as from about 0.5%, 2% or 4% to about 5%, 10% or 20% including all combinations of such ranges. However, in certain notable embodiments, compositions of the present invention are substantially free of oils, and in certain other embodiments substantially free of both oils and waxes.

Surfactants and Dispersants

The film-forming polymer portion may provide sufficient thickening of the vehicle to obviate the need for dispersants or suspending agents. However, according to certain embodiments of the present invention, the mascara composition may further optionally include a surfactant or dispersant, primarily to assist in wetting or dispersing of the particulate portion. Any surfactants, including anionic, nonionic, amphoteric, and cationic, surfactants, may be used in the present invention, as long as the surfactant is cosmetically or dermatologically acceptable. The surfactant may be used either singly or in combination two or more thereof. In one embodiment, the mascara composition may include an anionic surfactant/dispersant such as sodium laureth sulfate.

If present, the amount of the surfactant or dispersant may be from about 0.1 to about 5% by weight. In certain other embodiments the concentration of dispersants and surfactants is limited to less than 1%, such as less than about 0.5%, such as less than about 0.1%.

Colorants and Particulates

Mascara compositions of the present invention may optionally include at least one colorant. Suitable colorants include, but are not limited to inorganic particulates that impart color or optical effects and organic pigments. Particulate materials are generally finely divided particulates that are insoluble in but are otherwise homogeneously stabilized (suspended or dispersed) in a vehicle of the composition. The one or more particulate materials are typically materials that are incapable of chemically "self-fusing" in-use and are not themselves film-forming.

Suitable inorganic particulate materials include any of a variety of porous, semi-porous, non-porous, or hollow, coated or uncoated water-insoluble inorganic particulates such as silica, alumina, carbon and any of various oxides, silicates, aluminosilicates, nitrides, carbides, carbonates, and the like. In particular embodiments, the inorganic particulate is selected from carbon black, silica, and iron oxide. Other particulates, e.g., organic pigments such as lake pigments; other organic particulates such as polymeric particulates including nylon particulates, acrylate particulates (e.g., PMMA), silicone elastomer particulates, and the like may also be used. The concentration by weight of colorant in the mascara may range from about 0.25%, 0.5% or 1% to about 5%, 10%, or 15%.

Any of various lipophilic or water soluble dyes may be used as well. Typically, when the composition contains colorants, the composition may be used as a mascara composition. Alternatively, when the composition does not contain colorants, it is a clear or transparent composition which can be used as a basecoat (or topcoat) prior to (or after) application of a mascara composition to keratinous materials. A composition free of colorants may also be used as a solitary coating (without an additional separate basecoat or topcoat). However, it is possible that topcoats or basecoats could contain colorants, and/or that a mascara composition could contain little or no colorant.

Vehicle

In order to facilitate application to the eyelashes, mascaras of the present invention generally include a vehicle in which the film-forming polymer portion is stabilized (i.e., dissolved, dispersed or suspended). The vehicle generally includes, consists of or consists essentially of water. In certain embodiments of the invention, the mascara compositions of the present invention include at least about 30% water, such as from about 40% to about 90%, such as from about 45% to about 85%, such as from about 60% to about 80% water.

Additional Ingredients

The mascara composition of the present invention may further include various additives desirably used in cosmetic or dermatological compositions. For example, water, thickeners, dispersants, anti-oxidants, pH adjusters, preservatives, neutralizing agents, fragrances, fillers, co-solvents, plasticizers, cosmetic and dermatological active agents such as emollients, moisturizers, vitamins, UV filters, and sunscreens, and mixtures thereof can be added. A non-exhaustive listing of such ingredients can be found in the CTFA *International Cosmetic Ingredient Dictionary and Handbook*, Fourteenth Edition (2012), contents of which are incorporated herein by reference in its entirety.

One skilled in the art will take care to select the optional additional additives and/or the amount thereof such that the advantageous properties of the mascara compositions according to the present invention are not, or are not substantially, adversely affected by the envisaged addition.

These substances may be selected variously by one skilled in the art to prepare a composition which has the desired properties, for example, consistency or texture.

According to certain embodiments mascaras of the present invention are substantially free of polyhydric alcohols such as glycerin or glycols such as propylene, butylene or hexylene glycol.

According to certain embodiments, the mascara composition of the present invention is in the form of a water solution or dispersion where the non-ionic water-soluble or water dispersible copolymer comprising a cyclic amide monomer, a cyclic amine monomer, and an acrylamide monomer, the at least one secondary film-forming polymer, the C2-C5 alcohol and one or more optional ingredients are present as dissolved or dispersed in a vehicle that includes water. According to certain embodiments mascara compositions of the present invention have a viscosity from about 0.01 kPa·s, 0.1 kPa·s or 0.3 kPa·s to about 0.6 kPa·s, 10 kPa·s or 50 kPa·s including all combinations of such ranges, when measured at a shear rate of 1 s$^{-1}$ as measured using, for example, the AR-G2 magnetic bearing rheometer, available from TA Instruments of New Castle, Del. In order to adjust the viscosity of the mascara formulation, one may use one or more viscosity modifiers. According to certain other embodiments of the invention, the mascara may have a pH that is from about 5 to about 8.

The mascara composition of the present invention is intended to be applied onto keratinous materials such as keratin fibers, in particular, eyelashes or eyebrows. In certain notable embodiments the mascara is applied to a portion of keratinous surface that one desires to adopt a concave curvature. In particular, the inventors have found that compositions of the present invention are useful for self-curling. When used in this regard, the mascara is applied to the top surface of the upper eyelash and allowed to dry. By applying only to the top surface of the lashes, the lash will curl upwards upon drying.

As described above, according to one aspect of the present invention, the mascara composition has improved cosmetic properties such as, for example, increased volume properties, increased self-curling properties, increased self-curl retention properties, increased length properties, and the like.

Methods of Making

Mascara compositions of the present invention may be made by mixing at least one non-ionic, water-soluble or water-dispersible copolymer including a cyclic amide monomer, a cyclic amine monomer, and an acrylamide monomer in water until dissolution. This polymer and other water-soluble ingredients may be mixed by stirring, shaking, grounding, or beating, optionally with a stirrer, a magnetic stirrer, a shaker, a homogenizer, or any other methods suitably used to mix cosmetic composition. The mixing may be carried out with or without heating or cooling the ingredients. Particulates and other ingredients that are to be dispersed are then added with mixing to form a homogeneous mixture.

One embodiment of the present invention provides a method of improving curl of keratinous materials. The mascara composition described above is applied onto the keratinous materials. The keratinous materials are preferably keratin fibers, in particular eyelashes and eyebrows, but especially eyelashes. The mascara composition is applied onto the keratinous materials in an amount sufficient to improve the curl of the keratinous materials. To improve the curl of keratin fibers, the mascara composition may be applied onto the keratin fibers in an amount sufficient to increase the curl, and also a volume and/or length of the keratin fibers. The mascara is applied to a portion of keratinous surface that one desires to adopt a concave curvature, such as the top surface of the upper eyelash and allowed to dry. Accordingly, the mascara compositions may be brushed or applied onto the eyelashes with attentiveness to apply it predominantly on the top surface of the top eyelashes rather than the bottom surface of the top eyelashes.

The manner or tool by which the mascara composition is applied onto the keratinous materials is not limited. Preferably, the mascara composition is applied onto keratin fibers by a brush, a wand, or a comb.

The compositions may be applied to eyelashes as needed, preferably once or twice daily, more preferably once daily and then preferably allowed to dry before subjecting to contact such as with clothing or other objects.

In certain embodiments, compositions of the present invention may be used as a "primer" (first treatment in a two-step process) such as before using as a second step a traditional mascara that includes wax. The second step may include applying the mascara of the second step to a bottom surface of the lashes or to top and bottom of the lashes.

Notwithstanding that the numerical ranges and parameters setting forth the broad scope of the invention are approximations, the numerical values set forth in the specific examples are reported as precisely as possible. Any numerical value, however, inherently contain errors necessarily resulting from the standard deviation found in their respective measurements.

Examples Mascara Compositions

Mascara compositions were prepared. A premix consisting of about 20% of a film forming polymer portion, less than 5% of various functional ingredients (thickener, preservative, pigment, antioxidant), and the remainder water (hereinafter, "Premix"). The primary film forming polymer is a copolymer of N-vinyl pyrrolidone, methacrylamide, and N-vinylimidazole. In the premix, the film-forming polymer portion consists of about 95% primary film forming polymer and 5% of a secondary film-forming polymer (the secondary film-forming polymer in the Premix does not include cyclic amide monomer). To the Premix, various secondary film-forming polymers were added, as shown in Table 1.

The following SELF-CURLING TEST was performed on the various compositions. Using a flat iron, hair fiber strands (fake eyelashes), 12 mm in length secured between metal plates—available from SP Equation of Pourcieux, France—were straightened by gently stroking them using a commercially available hair straightener set to 450° F. for a sufficient period to straighten the fibers. Using a tongue depressor, various compositions to be tested were applied to the fake eyelashes and stroked ten times on one side of the simulated eyelashes. This deposits approximately 2 mg to 10 mg of composition. The treated lashes were put into a humidity chamber (25%-45% RH and 32° C.) for 5 minutes. A curl measurement was then taken by placing a protractor near the eyelashes and visually estimating the angle of curl relative to the horizontal surface of the metal plate within which the fake eyelashes are secured.

The result was recorded as Initial Curl in Table 1, below:

TABLE 1

Examples

| Ref. | Formula | Secondary Film-Forming Polymer(s) | Ethanol (%) | Initial Curl (°) |
|---|---|---|---|---|
| Comp. Example C1 | 100% Premix | — | 0 | 25 |
| Comp. Example C2 | 95% Premix, 5% LUVIKSOL VA 73W[1] | VP/VA Copolymer[1] | 0 | 15-20 |
| Comp. Example C3 | 90% Premix, 10% LUVIKSOL VA 73W[1] | VP/VA Copolymer[1] | 0 | 10-15 |
| Comp. Example C4 | 95% Premix, 5% LUVIKSOL VA 64W[2] | VP/VA Copolymer[2] | 0 | 30 |
| Comp. Example C5 | 90% Premix, 10% LUVIKSOL VA 64W[2] | VP/VA Copolymer[2] | 0 | 10-20 |
| Example E1 | 95% Premix, 5% LUVIKSOL VA 73E[3] | VP/VA Copolymer[3] | 2.5 | 15-55 |
| Example E2 | 90% Premix, 10% LUVIKSOL VA 73E[3] | VP/VA Copolymer[3] | 5.0 | 20-40 |
| Example E3 | 95% Premix, 5% LUVIKSOL PLUS[4] | Polyvinyl caprolactam[4] | 3.0 | 20-50 |
| Example E4 | 90% Premix, 10% LUVIKSOL PLUS[4] | Polyvinyl caprolactam[4] | 6.0 | 10-30 |
| Comp. Example C6 | 95% Premix, 5% ADVANTAGE HC 37[5] | Vinylcaprolactam/ vinylpyrrolidone/ dimethylaminoethyl- acrylate copolymer[5] | 3.2 | 10-30 |
| Comp. Example C7 | 90% Premix, 10% ADVANTAGE HC 37[5] | Vinylcaprolactam/ vinylpyrrolidone/ dimethylaminoethyl- acrylate copolymer[5] | 6.4 | 20-60 |

[1]LUVIKSOL VA 73W, available from BASF of Ludwigshafen, Germany. 50% of 70% vinyl pyrrolidone/30% vinyl acetate polymer; 50% water
[2]LUVIKSOL VA 64W, available from BASF of Ludwigshafen, Germany. 50% of 60% vinyl pyrrolidone/40% vinyl acetate polymer; 50% water
[3]LUVIKSOL VA 73E, available from BASF of Ludwigshafen, Germany. 50% of 70% vinyl pyrrolidone/30% vinyl acetate polymer; 50% ethanol
[4]LUVIKSOL PLUS, available from BASF of Ludwigshafen, Germany. 40% of polyvinyl caprolactam; 60% ethanol
[5]ADVANTAGE HC 37, available from Ashland Inc of Kovington, KY. 37% vinylcaprolactam/vinyl pyrrolidone/dimethylaminoethylacrylate copolymer; 63% ethanol The results indicate that compositions including a non-ionic water-soluble or water dispersible copolymer that includes a cyclic amide monomer, a cyclic amine monomer, and an acrylamide monomer as well as a secondary nonionic secondary film-forming polymer having a fraction of a second cyclic amide monomer that is at least about 70% of the at least one secondary film-forming polymer and 0.5% to 5% ethanol have surprisingly good performance.

Furthermore, six additional mascara formulations were prepared. To the Premix various secondary film-forming polymers were added, including dimethicone copolymer. The results are shown in Table 2, below.

TABLE 2

Examples

| Ref. | Formula | Secondary Film-Forming Polymer(s) | Ethanol (%) | Initial Curl (°) |
|---|---|---|---|---|
| Comp. Example C1 | 100% Premix | — | 0 | 25 |
| Inventive Example E11 | 95% Premix, 1.5% LUVIKSOL VA 73E[3], 3.5% LUVIKSOL PLUS[4] | VP/VA Copolymer[3] and Polyvinyl caprolactam[4] | 2.9 | 20-40 |
| Inventive Example E12 | 94.5% Premix, 1.5% LUVIKSOL VA 73E[3], 3.5% LUVIKSOL PLUS[4], 0.5% DOWSIL HMW 2220[6] | VP/VA Copolymer[3] and Polyvinyl caprolactam[4] and Divinyl/dimethicone Copolymer[6] | 2.9 | 30-50 |
| Inventive Example E13 | 94% Premix, 1.5% LUVIKSOL VA 73E[3], 3.5% LUVIKSOL PLUS[4], 1% DOWSIL HMW 2220[6] | VP/VA Copolymer[3] and Polyvinyl caprolactam[4] and Divinyl/dimethicone Copolymer[6] | 2.9 | 25-50 |
| Inventive Example E14 | 90% Premix, 5% LUVIKSOL VA 73E[3], 5% LUVIKSOL PLUS[4] | VP/VA Copolymer[3] and Polyvinyl caprolactam[4] | 5.5 | 15-30 |
| Inventive Example E15 | 89% Premix, 5% LUVIKSOL VA 73E[3], 5% LUVIKSOL PLUS[4], 1% DOWSIL HMW 2220[6] | VP/VA Copolymer[3] and Polyvinyl caprolactam[4] and Divinyl/dimethicone Copolymer[6] | 5.5 | 15-40 |
| Inventive Example E16 | 90% Premix, 3% LUVIKSOL VA 73E[3], 7% LUVIKSOL PLUS[4], 1% DOWSIL HMW 2220[6] | VP/VA Copolymer[3] and Polyvinyl caprolactam[4] | 5.7 | 20-45 |

[3]LUVIKSOL VA 73E, available from BASF of Ludwigshafen, Germany. 50% of 70% vinyl pyrrolidone/30% vinyl acetate polymer; 50% ethanol
[4]LUVIKSOL PLUS, available from BASF of Ludwigshafen, Germany. 40% of polyvinyl caprolactam; 60% ethanol
[6]DOW CORNING DOWSIL HMW 2220 Non-Ionic Emulsion, available from Dow Corning of Midland, Michigan. 60% Divinyl/dimethicone Copolymer, water dispersion.

These results also indicate that compositions including a non-ionic water-soluble or water dispersible copolymer that includes a cyclic amide monomer, a cyclic amine monomer, and an acrylamide monomer as well as a secondary nonionic secondary film-forming polymer having a fraction of a second cyclic amide monomer that is at least about 70% of the at least one secondary film-forming polymer and 0.5% to 8% ethanol have surprisingly good performance. Furthermore, addition of the dimethicone copolymer provides an additional surprising boost in performance.

What is claimed is:

1. A mascara composition, comprising:
a vehicle comprising water;
a dimethicone copolymer, present in an amount >0% and ≤1% by weight;
a film-forming portion comprising
   a primary film-forming polymer that is a non-ionic and water-soluble or water dispersible copolymer comprising a first cyclic amide monomer, a cyclic amine monomer, and an acrylamide monomer, the primary film-forming polymer comprising at least about 50% by weight of the film-forming portion; and
   a plurality of nonionic secondary film-forming polymers; and
from about 0.5% to about 8% by weight of a $C_2$-$C_5$ alcohol,
wherein the plurality of at least one non-ionic secondary film-forming polymers comprises a first secondary film-forming polymer having vinyl pyrrolidone functionality and a second secondary film-forming polymer having vinylcaprolactam functionality, and
wherein at least one of the first secondary film-forming polymer or the second secondary film-forming polymer comprises a fraction of a second cyclic amide monomer that is at least about 70% by weight of the first secondary film-forming polymer or the second secondary film-forming polymer.

2. The mascara composition of claim 1, further comprising a polydimethylsiloxane/vinyl copolymer.

3. The mascara composition of claim 1 wherein the non-ionic and water-soluble or water dispersible copolymer is present in a concentration by weight that is from about 10 percent to about 60 percent.

4. The mascara composition of claim 1 wherein the non-ionic and water-soluble or water dispersible copolymer is present in a concentration by weight that is from about 10 percent to about 20 percent.

5. The mascara composition of claim 1 wherein the first cyclic amide monomer is a vinyl pyrrolidone.

6. The mascara composition of claim 1 wherein the cyclic amine monomer is an imidazole.

7. The mascara composition of claim 1 wherein the non-ionic and water-soluble or water dispersible copolymer is a copolymer of N-vinyl pyrrolidone, methacrylamide, and N-vinylimidazole.

8. The mascara composition of claim 1 wherein the second cyclic amide monomer is selected from a vinyl pyrrolidone, a vinylcaprolactam, and combinations thereof.

9. The mascara composition of claim 1 wherein the first secondary film-forming polymer having vinyl pyrrolidone functionality is present in a concentration by weight of first secondary film-forming polymer and the second secondary film-forming polymer having vinylcaprolactam functionality is present in a concentration by weight of second secondary film-forming polymer and wherein the concentration by weight of first secondary film-forming polymer is less than the concentration by weight of second secondary film-forming polymer.

10. The mascara composition of claim 1, wherein the film-forming polymer portion comprises about 60% to about 90% by weight of the primary film-forming polymer and from about 5% to about 40% of the plurality of non-ionic secondary film-forming polymers.

11. The mascara composition of claim 1, wherein the mascara composition is substantially free of wax.

12. The mascara composition of claim 1, wherein the mascara composition is substantially free of oil.

13. A mascara composition, comprising:
from about 40% to about 90% by weight of water;
a film-forming portion comprising
   a primary film-forming polymer that is a non-ionic and water-soluble or water dispersible copolymer comprising a first cyclic amide monomer, a cyclic amine monomer, and an acrylamide monomer, the primary film-forming polymer comprising at least about 50% by weight of the film-forming portion; and
   two or more other polymers, including
      a first secondary film-forming polymer having a fraction of a second cyclic amide monomer that is at least about 70% by weight, wherein the first secondary film-forming polymer is non-ionic; and
      a second secondary film-forming polymer which is a dimethicone copolymer present in an amount >0% and ≤1% by weight of the mascara composition; and
   from about 0.5% to about 8% by weight of ethanol,
wherein the first secondary film-forming polymer has vinyl pyrrolidone functionality.

14. A method of applying makeup to the eyelashes, comprising applying directly to a top surface of eyelashes the mascara composition of claim 1.

15. The mascara composition of claim 1, wherein the mascara composition comprises less than about 1% by weight of dispersants and surfactants.

16. The mascara composition of claim 1, wherein the primary film forming polymer is present in an amount between about 75% and about 95% by weight of the film-forming portion.

17. The mascara composition of claim 13, wherein the primary film forming polymer is present in an amount between about 75% and about 95% by weight of the film-forming portion.

* * * * *

UNITED STATES PATENT AND TRADEMARK OFFICE
CERTIFICATE OF CORRECTION

PATENT NO.          : 10,987,298 B2
APPLICATION NO.     : 16/022820
DATED               : April 27, 2021
INVENTOR(S)         : Christopher Pang et al.

Page 1 of 1

It is certified that error appears in the above-identified patent and that said Letters Patent is hereby corrected as shown below:

In the Claims

Claim 1, Line 17, delete the following: "at least one"

Signed and Sealed this
Twenty-ninth Day of June, 2021

Drew Hirshfeld
*Performing the Functions and Duties of the
Under Secretary of Commerce for Intellectual Property and
Director of the United States Patent and Trademark Office*